United States Patent [19]

Carganico et al.

[11] Patent Number: 5,204,364
[45] Date of Patent: Apr. 20, 1993

[54] N-IMIDAZOLYL- AND N-IMIDAZOLYLMETHYL-DERIVATIVES OF SUBSTITUTED BICYCLIC COMPOUNDS

[75] Inventors: Germano Carganico; Paolo Cozzi; Antonio Pillan, all of Milan; Patricia Salvati, Arese; Corrado Ferti, Barlassina, all of Italy

[73] Assignee: Farmitalia Carlo Erba, S.r.l., Milan, Italy

[21] Appl. No.: 499,390

[22] PCT Filed: Oct. 3, 1989

[86] PCT No.: PCT/EP89/01159
§ 371 Date: Jun. 27, 1990
§ 102(e) Date: Jun. 27, 1990

[87] PCT Pub. No.: WO90/03970
PCT Pub. Date: Apr. 19, 1990

[30] Foreign Application Priority Data

Oct. 6, 1988 [GB] United Kingdom ............... 8823488
Jan. 18, 1989 [GB] United Kingdom ............... 8901095
Jul. 27, 1989 [GB] United Kingdom ............... 8917201

[51] Int. Cl.$^5$ .............. A61K 31/415; C07D 233/56
[52] U.S. Cl. .............. 514/399; 548/335.1; 548/345.1; 548/311.4; 514/397
[58] Field of Search ............ 548/336, 335, 346; 514/397, 399

[56] References Cited

U.S. PATENT DOCUMENTS 3,485,917 12/1969 Godefroi et al. ............... 514/400
3,541,109 11/1970 Kauer ............... 260/309

(List continued on next page.)

FOREIGN PATENT DOCUMENTS 0000950 3/1979 European Pat. Off. .
0000951 3/1979 European Pat. Off. .

(List continued on next page.)

OTHER PUBLICATIONS

Carruthers, W. *Some modern methods of organic synthesis*, Second edition, Cambridge University Press, 1978, pp. 89–93.

(List continued on next page.)

*Primary Examiner*—Mary C. Lee
*Assistant Examiner*—Lenora Ava Miltenberger
*Attorney, Agent, or Firm*—Nikaido, Marmelstein, Murray & Oram

[57] ABSTRACT

The present invention relates to new N-imidazolyl and N-imidazolylmethyl derivatives of bicyclic compounds having the general formula (I)

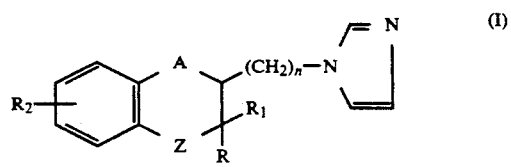

Wherein
A is a $\geq CR_3$ or $>CHR_3$ group, in which $R_3$ is hydrogen or $C_1$-$C_6$ alkyl, or a $>C=CR_4R_5$ group, in which each of $R_4$ and $R_5$ independently is hydrogen or $C_1$-$C_5$ alkyl;
Z is $-CH_2-$, $-O-$ or $-S-$;
n is zero or 1;
each of R and $R_1$ is independently hydrogen or $C_1$-$C_6$ alkyl;
$R_2$ is $-COCH_2OH$, $-CH_2OR'$, $-COOR'$, $-CONR'R''$ or $-CH=CH-COOR'$, in which each of $R'$ and $R''$ independently is hydrogen or $C_1$-$C_6$ alkyl, and the pharmaceutically acceptable salts thereof; and wherein:

a) when n is zero, then Z is $-CH_2-$ or $-O-$; whereas when n is one, then Z is $-CH_2-$, $-O-$ or $-S-$;
b) when A is $\geq CR_3$ or $>CHR_3$ in which $R_3$ is hydrogen, then n is one; and
c) when, at the same time, A is $>CHR_3$ in which $R_3$ is hydrogen, Z is $-CH_2-$, n is one and $R_2$ is $-COOR'$ wherein R' is as defined above, then at least one of R and $R_1$ is other than hydrogen, which are useful in the treatment of diseases related to an enhancement of $TxA_2$ synthesis.

8 Claims, No Drawings

U.S. PATENT DOCUMENTS

| | | | |
|---|---|---|---|
| 3,636,002 | 1/1972 | Godefroi | 548/346 |
| 3,637,731 | 1/1972 | Johnson | 548/346 |
| 3,992,403 | 11/1976 | Roebke | 548/347 |
| 4,006,243 | 2/1977 | Strehlke et al. | 514/399 |
| 4,115,578 | 9/1978 | Miller et al. | 514/397 |
| 4,118,461 | 10/1978 | Miller et al. | 514/397 |
| 4,150,153 | 4/1979 | Walker | 514/399 |
| 4,172,141 | 10/1979 | Walker | 514/399 |
| 4,218,461 | 8/1980 | Hoehn | 514/399 |
| 4,342,775 | 8/1982 | Cozzi et al. | 514/422 |
| 4,410,539 | 10/1983 | Cross et al. | 514/397 |
| 4,492,707 | 1/1985 | Cozzi et al. | 514/396 |
| 4,500,540 | 2/1985 | Hamilton et al. | 514/397 |
| 4,510,149 | 4/1985 | Cozzi et al. | 548/336 |
| 4,588,738 | 5/1986 | Cozzi et al. | 514/399 |
| 4,602,022 | 7/1986 | Cozzi et al. | 548/336 |
| 4,634,705 | 1/1987 | DeBernardis et al. | 514/256 |
| 4,777,257 | 10/1988 | Kanao | 548/341 |
| 4,808,627 | 2/1989 | Ogletree | 514/469 |
| 4,882,347 | 11/1989 | Cozzi et al. | 514/296 |

FOREIGN PATENT DOCUMENTS

| | | |
|---|---|---|
| 0003732 | 9/1979 | European Pat. Off. |
| 0135177 | 3/1985 | European Pat. Off. |
| 0297593 | 1/1989 | European Pat. Off. |
| 0298465 | 1/1989 | European Pat. Off. |
| 1445707 | 8/1976 | United Kingdom |
| 2071655 | 9/1981 | United Kingdom |
| 2071655A | 9/1981 | United Kingdom |
| 2122997 | 1/1984 | United Kingdom |
| 91/00102 | 1/1991 | World Int. Prop. O. |

OTHER PUBLICATIONS

Derwent Farmdoc 12191 K/06 (1983).
Derwent Farmdoc 47504C/27 (1979).
Derwent Farmdoc 85-001143/01 (1985).
86-246740/38, European Pharmaceuticals 21 (1990).
Derwent Farmdoc 87-258219/37 (1987).
Derwent Farmdoc 25602 K/11 (1983).
Derwent Farmdoc 67750 C/39 (1979).
Current Cardiovascular Patents/Fast Alert 14 (1989).
89-372193/51 European Pharmaceuticals 12 (1989).
C.A. 92:58775x (1980).
C.A. 91:57013q (1979).
84-070786/12 Pharmaceuticals p. 2 (1984).
Derwent Farmdoc 64584 C/37 (1979).
Derwent Farmdoc 61804B/34 (1979).
C.A. 84:180226u (1976).
C.A. 88:146091u (1978).
C.A. 86:1093v (1977).
C.A. 94:121527b (1981).
C.A. 94:103374v (1981).
Strehlke et al., 308 *Arch Pharm.* 94–109 (1975).
C.A. 79:5295r (1973).
Derwent Farmdoc 72472w (1975).
Derwent Farmdoc 28979F (1966).
C.A. 80:146166g (1974).
C.A. 94:24746q (1981).
C.A. 107:154283j (1987).
Derwent Farmdoc 21811 D/13 (1979).
Derwent Farmdoc 52738E/26 (1980).
Derwent Farmdoc 03708C (1978).
Derwent Farmdoc 23098 K/10 (1981).
Chemical Abstracts, vol. 106, No. 7, 43994b, 16 Feb. 1987.
Chemical Abstracts, vol. 95, No. 21, 187256q, 23 Nov. 1981.
Chemical Abstracts, vol. 107, No. 11, 96722p, 14 Sep. 1987.
Derwent Farmdoc 14731C/09 (1978).
C.A. 87:68100J (1977).
C.A. 89:197464W (1978).

N-IMIDAZOLYL- AND N-IMIDAZOLYLMETHYL-DERIVATIVES OF SUBSTITUTED BICYCLIC COMPOUNDS

The present invention relates to new N-imidazolyl and N-imidazolylmethyl derivatives of bicyclic compounds, in particular to N-imidazolyl and N-imidazolylmethyl derivatives of 3,4-dihydro-2H-1-benzopyran, 2H-1-benzopyran, 3,4-dihydro-2H-1-benzothiopyran, 2H-1-benzothiopyran, 1,2,3,4-tetrahydronaphthalene and 1,2-dihydronaphthalene, to a process for their preparation, to pharmaceutical compositions containing them and to their use as therapeutic agents.

The present invention provides novel compounds having the general formula (I)

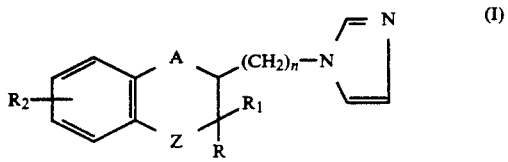

wherein
A is a $\geq CR_3$ or $>CHR_3$ group, in which $R_3$ is hydrogen or $C_1-C_6$ alkyl, or a $>C=CR_4R_5$ group, in which each of
$R_4$ and $R_5$ independently is hydrogen or $C_1-C_5$ alkyl;
Z is $-CH_2-$, $-O-$ or $-S-$;
n is zero or 1;
each of R and $R_1$ is independently hydrogen or $C_1-C_6$ alkyl;
$R_2$ is $-COCH_2OH$, $-CH_2OR'$, $-COOR'$, $-CONR'R''$ or $-CH=CH-COOR'$, in which each of R' and R'' independently is hydrogen or $C_1-C_6$ alkyl, and the pharmaceutically acceptable salts thereof; and wherein:
a) when n is zero, then Z is $-CH_2-$ or $-O-$; whereas when n is one, then Z is $-CH_2-$, $-O-$ or $-S-$;
b) when A is $\geq CR_3$ or $>CHR_3$ in which $R_3$ is hydrogen, then n is one; and
c) when, at the same time, A is $>CHR_3$ in which $R_3$ is hydrogen, Z is $-CH_2-$, n is one and $R_2$ is $-COOR'$ wherein R' is as defined above, then at least one of R and $R_1$ is other than hydrogen.

The above proviso a) excludes from formula (I) compounds wherein n is zero and Z is $-S-$, that are not obtainable according to the processes herein described. The proviso b) excludes the compounds previously disclosed by U.S. Pat. Nos. 4,510,149 and 4,602,022; and proviso c) excludes those disclosed by E.P.-A-135177.

The invention also includes within its scope all the possible isomers, stereoisomers and their mixtures and the metabolites and the metabolic precursors or bioprecursors of the compounds of formula (I). A $C_1-C_6$ alkyl or $C_1-C_5$ alkyl group is preferably a $C_1-C_4$ alkyl group, in particular methyl, ethyl, propyl and isopropyl, more preferably methyl and ethyl.

The substituent $R_2$ can be linked to any of the carbon atoms of the benzene moiety.

Pharmaceutically acceptable salts of the compounds of the invention include acid addition salts, with inorganic, e.g. nitric, hydrochloric, hydrobromic, sulfuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium, bases, or with organic bases, e.g. alkylamines, preferably triethylamine.

As stated above the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I). Preferred compounds of the invention are the compounds of formula (I), wherein, subject to the above provisos,
A is a $\geq CR_3$ or $>CHR_3$ group in which $R_3$ is $C_1-C_4$ alkyl, or a $>C=CHR_4$ group in which $R_4$ hydrogen or $C_1-C_4$ alkyl; Z is $-CH_2-$, $-O-$ or $-S-$;
n is zero or 1;
R and $R_1$ are hydrogen;
$R_2$ is $-COCH_2OH$, $-CH_2OR'$, $-COOR'$, $-CONR'R''$ or $-CH=CH-COOR'$, in which each of R' and R'' independently is hydrogen or $C_1-C_4$ alkyl; and the pharmaceutically acceptable salts thereof.

More preferred compounds of the invention are the compounds of formula (I), wherein, subject to the above provisos,
A is a $\geq CR_3$ group in which $R_3$ is $C_1-C_4$ alkyl, or a $>C=CH_2$ group;
Z is $-CH_2-$;
n is zero or 1;
R and $R_1$ are hydrogen;
$R_2$ is $-COOR'$, wherein R' is hydrogen or $C_1-C_4$ alkyl; or $-CONH_2$; and the pharmaceutically acceptable salts thereof.

Examples of preferred compounds of formula (I) are the following:
5,6-dihydro-7-(1H-imidazol-1-yl)-8-methyl-2-naphthalenecarboxylic acid;
5,6-dihydro-8-ethyl-7-(1H-imidazol-1-yl)-2-naphthlenecarboxylic acid;
5,6-dihydro-7-(1H-imidazol-1-ylmethyl)-8-methyl-2-naphthalenecarboxylic acid;
5,6,7,8-tetrahydro-7-(1H-imidazol-1-ylmethyl)-8-methyl-2-naphthalenecarboxylic acid;
ethyl 5,6-dihydro-7-(1H-imidazol-1-yl)-8-methyl-2-naphthalenecarboxylate;
5,6-dihydro-7-(1H-imidazol-1-yl)-8methyl-2-naphthalenecarboxamide;
ethyl 5,6-dihydro-7-(1H-imidazol-1-ylmethyl)-8-methyl-2-naphthalenecarboxylate;
5,6-dihydro-8-ethyl-7-(1H-imidazol-1-ylmethyl)-2-naphathalenecarboxylic acid; and
7,8-dihydro-6-(1H-imidazol-1-ylmethyl)-5-methyl-2-naphthalenecarboxylic acid;
and the pharmaceutically acceptable salts thereof.

The compounds of the invention and the salts thereof can be prepared by the process comprising:
a) submitting to β-elimination a compound of formula (II)

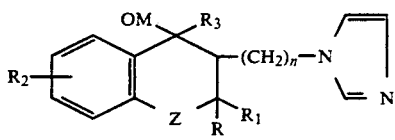

(II)

wherein R, $R_1$, $R_2$, $R_3$, n and Z are as defined above the M represents hydrogen or an acyl group, thus obtaining a compound of formula (I), wherein A is a $\geq C-R_3$ group, in which $R_3$ is as defined above; or b) alkylenating a compound of formula (III)

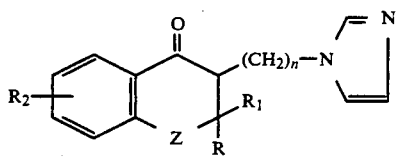

(III)

wherein R, $R_1$, $R_2$, Z and n are as defined above, thus obtaining a compound of formula (I) in which A is a $>C=CR_4R_5$ group, wherein $R_4$ and $R_5$ are as defined above; or c) reducing a compound of formula (IV)

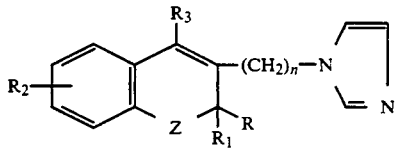

(IV)

wherein R, $R_1$, $R_2$, $R_3$, n and Z are as defined above, thus obtaining a compound of a formula (I), wherein A is a $>CHR_3$ group in which $R_3$ is as defined above; or d) isomerizing a compound of formula (V)

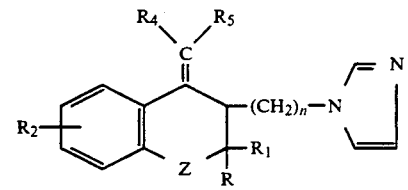

(V)

wherein R, $R_1$, $R_2$, n and Z are as defined above, one of $R_4$ and $R_5$ is hydrogen or $C_1$-$C_5$ alkyl, the other being hydrogen; and wherein when n is zero, Z is $-CH_2-$ or $-O-$, and when n is one, Z is $-CH_2-$, $-O-$ or $-S-$, thus obtaining a compound of formula (I) wherein A is a $\geq CR_3$ group in which $R_3$ is a $C_1$-$C_6$ alkyl; and if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of compounds of formula (I) into the singles isomers.

When M in a compound of formula (II) is a acyl group, it is, for example, a $C_2$-$C_4$ carboxylic acyl group, in particular acetyl, or it may be a mesyl or tosyl group. β-elimination on a compound of formula (II), according to process a) reported above may be carried out in the presence of a suitable organic solvent, such as glacial acetic acid, mixtures of acetic anhydride-pyridine, dimethylformamide (DMF) or dimethylsulfoxide (DMSO), or benzene, in the presence of suitable amounts, even catalytic amounts, of a strong acid, e.g. concentrated $H_2SO_4$, HCl, or p-toluene-sulphonic acid, at temperatures ranging from about 50° C. to the reflux temperature. The same conversion may also be performed by refluxing a compound of formula (II) in concentrated acids, e.g. hydrochloric, trifluoroacetic or hydrobromic acid. When in a compound of formula (II) M is an acyl group, in particular, acetyl, the reaction may also be carried out by pyrolysis, at temperatures ranging, preferably, from about 200° C. to about 300° C.

Alkylenation, i.e. olefination, of a compound of formula (III) may be performed by following known methods, e.g. by Wittig reaction or Horner-Emmons reaction. For example a compound of formula (III) may be reacted with a phosphonium salt of formula (VI)

(VI)

wherein $R_4$ and $R_5$ are as defined above; Q is a aryl group, in particular a phenyl group; and Hal is halogen, preferably iodine or bromine.

The reaction of a compound of formula (III) with a compound of formula (VI) can be carried out in the presence of a strong basic agent, such as a $C_1$-$C_6$ alkyllithium, preferably butyllithium; phenyllithium; a sodium or potassium alkoxide, preferably potassium tert.butylate; sodium amide or sodium hydride. The reaction may be performed in a suitable organic solvent, e.g. tetrahydrofuran, dioxane, dimethyl sulfoxide, N,N-dimethylformamide, benzene or a lower alkanol; at temperatures preferably ranging from about −60° C. to about 90° C.

Alternatively a compound of formula (III) may be reacted with a phosphonate of formula (VII)

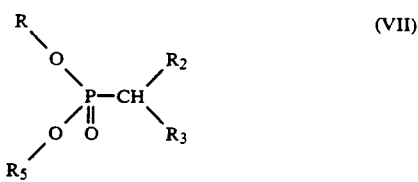

(VII)

wherein $R_2$ and $R_3$ are as defined above and $R_5$ is e.g. $C_1$-$C_6$ alkyl, preferably methyl or ethyl, or phenyl.

The reaction of a compound of formula (II) with a compound of formula (VII) may be performed by following the same procedure described as to the reaction of a compound of formula (II) with a compound of formula (VI). Reduction of compounds of formula (IV) to obtain a compound of formula (I), according to processes c), may be performed, for example, by catalytic hydrogenation in the presence of suitable catalyst, e.g. palladium, platinum, $PtO_2$, ruthenium or Raney-nickel in a suitable organic solvent, preferably chosen from a lower alkanol, e.g. methanol or ethanol, hydrochloric acid, acetic acid, cyclohexane, n-hexane, ethyl acetate, benzene, toluene or mixtures thereof, operating at a pressure ranging from atmospheric pressure to about 30 atmospheres and at temperatures ranging from room temperature to about 100° C. Isomerization of a compound of formula (V) to obtain a compound of formula (I), according to process d), may be performed by known methods, for example by heating in a strong arganic acid, for example trifluoroacetic acid or p.toluenesulfonic acid, or in a mineral acid, e.g. sulforic acid, or a Lewis acid, e.g. AlCl$_3$. The reaction may be performed by using the same acid as solvent or in an organic solvent chosen for example from benzene, toluene or acetate acid, at temperatures ranging preferably from about 60° C. to 120° C.

A compound of formula (I) may be converted, if desired, into another compound of formula (I).

These optional conversions may be carried out by methods known in themselves.

A compound of formula (I) containing an esterified carboxy group, may be converted into a compound of formula (I) containing a free carboxy group, by acidic or alkaline hydrolysis, operating at temperature ranging from the room temperature to about 100° C.

A compound of formula (I) containing a free carboxy group, may be converted into a compound of formula (I) containing an esterified carboxy group by esterification, e.g. via the corresponding acid halide, e.g. chloride, reacting with an excess of a suitable C$_1$–C$_6$ alkyl alkohol, or by direct esterification by means of acidic catalysis i.e. in the presence of dry HCl or SOCl$_2$ or BF$_3$-etherate. A compound of formula (I) containing a carbamoyl group may be converted into a compound of formula (I) containing a free carboxy group by hydrolysis, preferably by acid hydrolysis, in a suitable solvent, such as water, or by treatment with NaNO$_2$ and an aqueous strong inorganic acid, i.e. H$_2$SO$_4$, operating at temperatures ranging between the room temperature and 100° C.

A compound of formula (I) containing a free or esterified carboxy group may be converted into a compound of formula (I) containing a

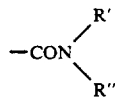

group, wherein R' and R" are as defined above.

Accordingly, the conversion of an esterified carboxy group into the corresponding amide may be performed by direct reaction with ammonia or an appropriate amine in a suitable aprotic solvent, e.g., ether or benzene or using an excess of the amine as solvent, at temperatures ranging from room temperature to reflux.

The conversion of free carboxy group into the corresponding amides may be carried out via an intermediate reactive derivative which may be isolated or not.

Intermediate reactive derivatives may be active esters e.g. NO$_2$-phenyl esters, or N-hydroxysuccinimide ester acid halides, preferably chloride, mixed anhydrides, e.g. ethoxycarbonyl or tert-butylcarbonyl anhydrides, or the reactive intermediate obtained in situ by reaction of the acid with dicyclohexylcarbodimide or carbonyl-diimidazole.

The reactive intermediates obtained following conventional ways, as those usually employed in the synthesis of peptides, are reacted with ammonia or an appropriate amine in a suitable solvent or with an excess of the amine itself at temperatures ranging from about −10° C. to about 50 ° C.

A compound of formula (I) wherein R$_2$ is a free or esterified carboxy group, in particular a lower alkoxycarboxyl group, may be converted into a compound of formula (I) wherein R$_2$ is a —CH$_2$OH group by reduction in conventional ways, preferably with LiAlH$_4$ in a suitable solvent, e.g. ethylether or THF.

The optional salification of a compound of formula (I) as well as the conversion of a salt into the free compound and the separation of a mixture of isomers into the single isomers may be carried out by conventional methods.

For example the separation of a mixture of geometric isomers, e.g. cis- and trans-isomers, may be carried out by fractional crystallization from a suitable solvent or by chromatography, either column chromatography or high pressure liquid chromatography.

A compound of formula (II), wherein M and R$_3$ are hydrogen, may be obtained by reducing a compound of formula (III)

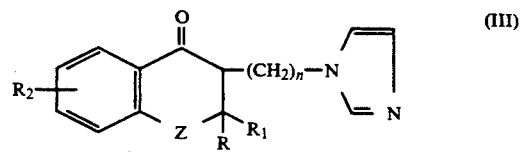

wherein Z, R, R$_1$, R$_2$ and n are as defined above, according to well known procedures, for example, by treatment with an alkali metal borohydride, e.g. NaBH$_4$, in a suitable solvent, e.g. methyl or ethyl alcohol or a mixture of water and ethyl alcohol, or by treatment with LiAlH$_4$ in an anhydrous solvent, e.g. diethyl ether or tetrahydrofuran, at a temperature ranging, in both cases, preferably between 0° C. and the reflux temperature, for reaction times varying approximately from 1 to 6 hours. A compound of formula (II), wherein M represents hydrogen and R$_3$ is C$_1$–C$_6$ alkyl, may be obtained by reacting a compound of formula (III), as defined above, with a compound of formula R$_3$—Mg—X, wherein R$_3$ is C$_1$–C$_6$ alkyl and X is a halogen atom, in particular chlorine or bromine. The reaction can be performed according to well known procedures for the Grignard reaction, e.g. by operating at temperatures ranging from about −78° C. to the reflux temperature, preferably from about −10° C. to about 30° C., in a suitable anhydrous solvent, e.g. diethyl ether or tetrahydrofuran, for reaction times ranging approximately from 1 to 6 hours.

A compound of formula (II), wherein M represents an acyl group, as defined above, may be obtained according to known methods, e.g. by reacting a compound of formula (II) wherein M is hydrogen, with the suitable acyl or sulfonyl halide, preferably chloride, for example, with acetyl chloride or with tosyl or mesyl chloride operating e.g. in anhydrous pyridine or in an inert solvent, e.g. anhydrous benzene, if desired in the presence of an equimolar amount of a base such as triethylamine, at temperatures ranging from room temperature to about 60° C. Alternatively, a compound of formula (II), wherein M represents hydrogen, n is zero and R, R$_1$, R$_2$, R$_3$ and Z are as defined above, may be obtained by reacting a compound of formula (VIII)

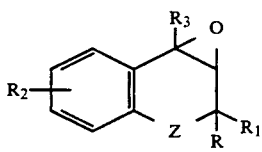 (VIII)

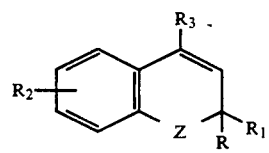 (X)

wherein R, $R_1$, $R_2$, $R_3$ and Z are as defined above, with imidazole or a salt thereof, which is preferably an alkali metal, e.g. sodium or potassium salt, or a silver salt. The reaction is preferably carried out either a) in the absence of solvent, at a temperature preferably ranging between the room temperature and about 180° C. and for reaction times which may vary from some minutes to about 20 hours using, if necessary, an excess of imidazole or a salt thereof, or b) in the presence of a suitable solvent, preferably dimethylformamide, dimethylacetamide, hexamethylphosphorotriamide, benzene, toluene, ethyl acetate, ethyl alcohol, dioxane or acetone, at a temperature preferably ranging between about 0° C. and the reflux temperatures, for reaction times varying from some minutes to about 12 hours.

The compounds of formula (III) wherein n is zero are known compounds or may be prepared following known procedures, e.g. those described in J. Het. Chem. (1984), 21; 311; J. Het. Chem. (1985) 22, 441 and J; Med. Chem. (1986), 26, 404.

The compounds of formula (III), wherein n is one, may be prepared according to known procedures, e.g. by a process comprising the reaction of a Mannich base of formula (IX)

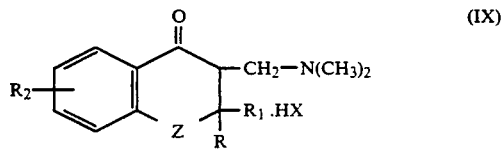 (IX)

wherein R, $R_1$, $R_2$ and Z are as defined above and X is chlorine or bromine, with imidazole.

This reaction may be carried out in water or water-alcohol mixtures preferably in water-ethanol or water-methanol mixtures, at temperatures ranging from room temperature to reflux. The Mannich base of formula (IX) can be prepared by following known procedures, e.g. those reported and cited in Synthesis (1984), 694. The compounds of formula (IV) are compounds of formula (I) according to the present invention, in which the symbol A is a $\geq CR_3$ group and can be obtained by process a) described above.

Also the compounds of formula (V) are compounds of formula (I), according to the present invention, wherein the symbol A is a $>C=CR_4R_5$ group and can be obtained by process b) described above.

Thence reduction of a compound of formula (IV), according to process c) and isomerization of a compound of formula (V), according to process d), described above, may be regarded as examples of optional conversions of a compound of formula (I) into another compound of formula (I). The compounds of formula (VIII) are either known compounds, or may be obtained by well known methods, for example by epoxidation of a compound of formula (X)

wherein R, $R_1$, $R_2$, $R_3$ and Z are as defined above.

The reaction is preferably carried out either a) by treating a compound of formula (X) with a suitable peroxide, e.g. hydrogen peroxide, or with a suitable peracid, e.g. peracetic acid or metachloroperbenzoic acid, in a suitable solvent, e.g. water or acetic acid, at a temperature ranging from 0° C. to room temperature and for reaction times varying from some minutes to 20 hours; or b) by treating a compound of formula (X) with halogen, preferably bromine, or N-halosuccinimide, preferably N-bromo-succinimide, in the presence of a catalytic amount of a base, e.g. potassium hydroxide, or an acid, e.g. hydrochloric acid, in a suitable solvent, e.g. water or tetrahydrofuran or water-tetrahydrofuran mixtures, at a temperature ranging from 0° C. to reflux temperature, for reaction times ranging from 1 hour to 20 hours, and treating the obtained crude halohydrin with a suitable base, e.g. sodium methoxide, in a suitable solvent, e.g. methanol, at a temperature ranging from room temperature to reflux, for reaction times varying from 1 hour to 12 hours.

The compounds of formula (VI), (VII) and (X) are known compounds or may be obtained by procedures well known in organic chemistry. When in the compounds of the invention and in the intermediate products thereof groups are present which need to be protected during the reactions reported above, the groups can be protected in conventional way before the reaction takes place and then deprotected after its end, according to well known methods.

PHARMACOLOGY

We have found that the compounds of formula (I), and the pharmaceutically acceptable salts thereof are selective inhibitors of thromboxane $A_2$ (Tx$A_2$) synthesis and are therefore useful in the treatment of diseases related in particular to an enhancement of Tx$A_2$ synthesis in mammals, including humans.

The compounds of formula (I) were for example tested for their ability to inhibit Tx$A_2$ synthase activity (as reflected by Tx$B_2$ generated in whole blood during clotting) in vitro in the rat.

Method

The effect of a representative group of compounds according to the present invention on Tx$B_2$ synthesis was evaluated in comparison with known products in whole blood of normal Sprague Dawley rats (Charles River Italy). Blood was withdrawn from the abdominal aorta of the animals under light ether anaesthesia. The blood was immediately divided in portions of 0.5 ml and distributed in glass tubes each containing a concentration of the test compound, or of the reference compounds.

Samples were then allowed to clot for 1 hour at 37° C., centrifuged at 3000 rpm for 10 min, serum collected and stored at −20° C. until assayed. Tx$B_2$ levels were determined by RIA according to previously described procedures (Thromb. Res. 17, 3/4, 317, 1980) using highly sensible antibody.

Table 1 herebelow shows that the compounds according to the present invention markedly inhibit $TxA_2$ synthesis in whole blood.

TABLE 1

In vitro effect on $TxB_2$ synthesis in normal rats.
Data are expressed as $IC_{50}$ (M) and limits for $p = 0.95$

| Compound | $IC_{50}$ (M) | LIMITS |
| --- | --- | --- |
| FCE 25672 | $2.9 \times 10^{-7}$ M | $(1.2 - 5.4 \times 10^{-7})$ |
| FCE 26333 | $4.3 \times 10^{-8}$ M | $(1.2 - 10 \times 10^{-8})$ |
| FCE 26252 | $7.4 \times 10^{-7}$ M | (not calculated) |
| FCE 22178 | $1.0 \times 10^{-6}$ M | $(0.56 - 1.6 \times 10^{-6})$ |
| ASA | $3.1 \times 10^{-5}$ M | $(2.6 - 3.8 \times 10^{-7})$ |

Internal code FCE 25672 means 5,6-dihydro-7-(1H-imidazol-1-yl)-8-methyl-2-naphthalenecarboxylic acid;
Internal code FCE 26333 means 5,6-dihydro-7-(1H-imidazol-1-ylmethyl)-8-methyl-2-naphthalenecarboxylic acid;
Internal codxe FCE 26252 means 5,6,7,8-tetrahydro-7-(1H-imidazol-1-yl)-8-methylene-2-naphthalenecarboxylic acid;
Internal code FCE 22178 means 5,6-dihydro-7-(1H-imidazol-1-yl)-2-naphthalenecarboxylic acid, which is known from US-A-4,510,149 and is a thromboxane synthase inhibitor;
Acetyl salicyclic acid (ASA) is a cyclooxygenase inhibitor.

The compounds of the invention, being able to inhibit selectively the formation of $TxA_2$, can be used as vasodilatory and antiaggregant agents, for example in all the cases of thrombosis, peripheral vasculopathies and coronary artery disease. In fact inhibition of $TxA_2$ production reduces the probability of thrombi formation and of vasoconstriction with consequent ischemic events and leaving unaltered (or increasing) $PGI_2$ production, improves vasodilation, tissue blood supplies and protects the vessel wall.

Another use of the compounds of the invention is for the treatment of migraine. As is known, for example, in the case of migraine it has been demonstrated a diffused vasoconstriction induced by platelet $TxA_2$ overproduction [J. Clin. Pathol. (1971), 24, 250; J. Headache (1977) 17, 101]. A platelet overproduction of $TxA_2$ and MDA (malondialdehye) in diabetes mellitus has been demonstrated and correlated with microcirculatory defects in the illness [Metabolism (1979) 28, 394; Eu. J. Clin. Invest. (1979) 9, 223; Thrombosis Haemost. (1979), 42, 983; J. Lab. Clin. Med. (1981) 97, 87]. Therefore, the compounds of the invention can be used in the treatment of diabetes, in particular, diabetic microangiopathy.

Moreover, the compounds of the invention can be used as anti-inflammatory agents. As is known, for example, fluid obtained from carrageenin-induced granuloma converts arachidonic acid into $TxA_2$ in vitro and $TxA_2$ levels are increased in the synovial fluid of rheumatoid arthritis patients and in the fluid of carrageenin-induced inflammation in rats [Prostaglands (1977), 13, 17; Scand. J. Rheum. (1977), 6, 151]. Recently it has been also demonstrated that an overproduction of $TxA_2$ is involved in the pathogenesis of hypertension and that a specific inhibitor of $TxA_2$ production may be employed in hypertension [Eu. J. Pharmacol. (1981), 70, 247]. In fact the compounds of the invention can be used as hypotensive agents.

For example an increased $TxA_2$ synthesis and decreased prostacyclin synthesis are reported in pregnancy-induced hypertension [Am. J. Obstet:Gynecol. (1987), 157, 325; Hypertension (1988), 11, 550]. Treatment with thromboxane synthase inhibitors is therefore useful in this pathology.

Furthermore it has been shown a role of $TxA_2$ in the pathogenesis of ulcerative disorders of the stomach in accordance with its powerful gastric vasoconstrictory activity, so that also in this field a $TxA_2$ inhibitor is useful [Nature (1981), 202, 472]. In fact the compounds of the invention are indicated for the treatment of peptic ulcers.

The compounds of the invention can be also antitumoral agents. It is known, for example, that a selective inhibition of $TxA_2$ synthesis has been demonstrated to reduce the number of lung metastases and to slow down tumor growth [Nature (1982), 295, 188].

In view of the correlation between $TxA_2$ synthesis and calcium transport, recently showed by some authors, specific $TxA_2$ synthetase inhibitors, such as the compounds of the invention, can also find use in the treatment of osteoporosis, e.g. post-menopausal osteoporosis [Prostaglandins (1981), 21, 401].

Moreover the compounds of the invention are indicated for the treatment of angina pectoris and heart failure. In this respect, it is known, for example, that high levels of $TxB_2$ have been found in patients with Prinzmetal's angina [Prostaglandins and Med. (1979), 2, 243] and in patients with recurrent angina attacks [Sixth Intern. Congress on Thrombosis, Monte Carlo October, 1980 Abs No. 140].

The platelet antiaggregatory activity of the compounds of the invention was evaluated in vitro and in vivo, for example, according to the modified methods of Born [Born G. V. R., Nature 194, 927 (1962)] and Silver [Silver M. J., Science 183, 1085 (1974)].

The compounds of this invention were found in vitro to have inhibitory activity on platelet aggregation induced by collagen or ADP (adenosine-5'-diphosphate) in platelet rich plasma of guinea pig [Dunkin Hantley Iva: PDH (SPF) Ivanovas GmBH, Germany].

Therefore the compounds of the invention may be useful in preventing or reducing platelet loss during extracorporeal circulation; for example during coronary artery bypass and graft procedures or during kidney dialysis. It has been moreover shown that circulatory shock, for example endotoxic and haemorragic shock, is associated with increased $TxA_2$ synthesis so that the compounds of the invention can be useful in these pathologies. Moreover, the compounds of the present invention can also be useful for the treatment of bronchial hyperreactivity in the therapy of asthma.

A role for $TxA_2$ in asthma can be inferred on the basis of its bronchoconstrictory activity in experimental animal models [Br. J. Pharmacol. (1984), 82 (3) 565]. An inhibitory activity of bronchospasm induced by Platelet Activating Factor (PAF) in rats is also reported, e.g. for the $TxA_2$ synthase inhibitors described in GB-B-2205494.

The compounds of the present invention can also find use in the treatment of nephropathies e.g. forms of glomerulonephritis, diabetic nephropathy or nephropathies secondary to systemic lupus erithematous (SLE), and in the prevention and/or treatment of Cyclosporin A-induced nephrosis. Accordingly the compounds of this invention can also be used for preventing and/or treating toxemia during pregnancy, typically preeclampsia, eclampsia and preeclamptic (eclamptic, eclamptogenic) toxemia.

Recently a positive correlation between enhanced intrarenal synthesis of $TxA_2$ and the progression of chronic glomerular disease has been demonstrated in different animal models of immune and non-immune renal damage and in humans [J. Clin. Invest. (1985) 75, 94, J. Clin. Invest. (1985), 76, 1011].

Accordingly, the $TxA_2$ synthase inhibitors recently described e.g. in GB-B-2205240 were found to be active in reducing proteinuria and creatinine serum levels in the doxorubicin induced nephrosis in rats and in reducing proteinuria and increasing the glomerular filtration rate (GFR) in the spontaneous focal glomureulosclerosis in the Milan Normotensive Strain (MNS) rats.

The compounds of the invention may be also used to inhibit the renal and cardiac transplant rejection. In fact after transplantation increased urinary $TxB_2$ excretion or whole blood $TxA_2$ synthesis have been reported both in man and rats [Lancet (1981), ii, 431; Transplantation (1987) 43, 346].

Another use of the compounds of the present invention is in the treatment of hyperlipidaemia, namely hypercholesterolaemia and hypertriglyceridaemia secondary to nephrotic syndrome.

Hyperlipidaemia is a common feature of nephrotic syndrome in man [New Engl. J. Med. (1983) 312 (24) 1544] and in addition elevated triglycerides and cholesterol levels are reported in animal models such as doxorubicin induced nephrotic syndrome [Expt. Mol. Pathology (1983), 39, 282]; elevated urinary albumin excretion has been suggested as the pathogenetic mechanisms [Kidney International (1987), 32, 813]. Also $TxA_2$ synthase inhibitors recently described in GB-B-2205240, e.g. proved to be active in reducing cholesterol and triglycerides in aged Milan Normotenisve Strain rats and in reducing triglycerides in doxorubicin treated rats.

It has also been shown that in cholesterol fed rabbit, an animal model of diet induced atherosclerosis, arachidonic acid metabolism is an important factor in early lesion development. In particular a shift in metabolism from $TxA_2$ to $PGE_2$ may suppress lesion development (i.e. atheromatous plaque) in hypercholesterolemia.

The compounds of invention can be therefore used in this pathology.

The compounds of the invention can also can also be used in associated with thrombolytic agents (e.g. tPA, Streptokinase, pro-Urokinase) in order to reduce the dose of the latter required in thrombolytic therapy, and to lower the incidence of reocclusion and possibly haemorrage.

The toxicity of the compounds of the invention is negligible, therefore they can be safely used in therapy. Mice and rats which had been deprived of food for nine hours were treated orally with single administrations of increasing doses of compounds of the invention, then housed and normally fed. The orientative acute toxicity ($LD_{50}$) was assessed on the seventh day after the treatment and e.g. in the compound added as FCE 26572, was higher than 800 mg/kg.

In view of their high therapeutic index the compounds of the invention can be safely used in medicine. The therapeutic regimen for the different clinical syndromes must be adapted to the type of pathology, taking into account, as usual, also the route of administration, the form in which the compound is administered and the age, weight and conditions of the subject involved. The oral route is employed, in general, for all conditions requiring such compounds. Preference is given to intravenous injection or infusion for the treatment of acute pathological states.

For maintenance regimens the oral or parenteral, e.g. intramuscular, route is preferred.

The dosage level suitable for oral administration to adult humans of the compounds of the invention e.g. 5,6-dihydro-7-(1H-imidazol-1-yl)-8-methyl-2-naphthalenecarboxylic acid, may range from about 50 mg to about 500 mg per dose 1 to 3 times a day.

Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions, or suspensions tablets, pills, gelatine capsules, syrups, drops or suppositories.

Thus, for oral administration, the pharmaceutical compositions containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpirrolidone; disaggregating agents, such as starches, alginic acid, alginates, sodium starch glycolate; effervescing mixtures; dyestuffs; sweeteners; wetting agents, such as lecithin, polysorbates, laurylsulphates; and in general, non-toxic and pharmacologically inactive substances used in pharmaceutical formulations. Said pharmaceutical preparations may be manufactured in known manner, for example by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injection or infusion may contains as carrier, for example, sterile water or preferably they may be in the form of sterile aqueous isotonic saline solutions.

The suppositories may contain together with the active compound a pharmaceutically acceptable carrier e.g. cocoa-butter, polyethylene glycol, a polyoxyethylene sorbitan fatty acid ester surfactant or lecithin.

The following examples illustrate but do not limit the present invention.

EXAMPLE 1

A solution of 5,6,7,8-tetrahydro-8-hydroxy-8-methyl-7-(1H-imidazol-1-yl)-2-naphthalenecarboxylic acid (4 g) in glacial acetic acid (50 ml) and concentrated sulfuric acid (12 ml) is heated at 80° C. for 4 hours.

After cooling, the reaction mixture is poured into 100 ml of ice-water, neutralized with ammonium hydroxide and extracted with ethyl acetate. The organic layer is dried over sodium sulfate and evaporated to dryness. The resulting crude product is chromatographed on silica gel (eluent CHCl$_3$:CH$_3$OH=90:10), giving 3.7 g of 5,6-dihydro-7-(1H-imidazol-1-yl)-8-methyl-2-naphthalenecarboxylic acid, m.p. 241°–243° C. (dec.).

Elemental analysis: Found: C 70.52; H 5.65; N 10.84. Calculated for C$_{15}$H$_{14}$N$_2$O$_2$: C 70.85; H 5.54; N 11.01.

N.M.R. (DMSO-d$_6$) ppm: 1.97 (3H, t, CH$_3$); 2.50–3.21 (4H, m, CH$_2$—CH$_2$); 7.00–8.00 (6H, m, phenyl and imidazole).

By proceeding analogously, the following compounds can be prepared:

5,6-dihydro-7-(1H-imidazol-1-ylmethyl)-8-methyl-2-naphthalenecarboxylic acid, m.p. 278°–80° C.
Elemental analysis: Found: C 70.05; H 5.98; N 10.39. Calculated for C$_{16}$H$_{16}$N$_2$O$_2$: C 71.62; H 6.01; N 10.44.

5.6-dihydro-8-ethyl-7-(1H-imidazol-1-yl)-2-naphthalenecarboxylic; acid;

3-(1H-imidazol-1-ylmethyl)-4-methyl-2H-1-benzothiopyran-6-carboxylic acid;

3-(1H-imidazol-1-ylmethyl)-4-ethyl-2H-1-benzopyran-6-carboxylic acid.

EXAMPLE 2

A solution of 1.9 g of 5,6-dihydro-7,8-epoxy-8-methyl-2-naphthalenecarboxylic acid (prepared by epoxidation of 5,6-dihydro-8-methyl-2-naphthalenecarboxylic acid, m.p. 150°–153° C.) in anhydrous DMF is added to a solution of imidazole potassium salt, prepared from prepared from 3.16 g of imidazole and 1.81 g of potassium, in anhydrous DMF (100 ml) and heated at 130° C., with vigorous stirring, for 6 hours. The solvent is evaporated under reduced pressure and the residue is taken up with water and ethyl acetate. The aqueous layer is separated and acidified to pH=5 with acetic acid. The water is evaporated under vacuum and the residue is chromatographed on silica gel (eluent CHCl$_3$:CH$_3$OH, 70:30) giving 1.6 g of 5,6,7,8-tetrahydro-8-hydroxy-8-methyl-7-(1H-imidazol-1-yl)-2-naphthalenecarboxylic acid.

EXAMPLE 3

A mixture of 5,6-dihydro-7(1H-imidazol-1-yl)-8-methyl-2-naphthalenecarboxylic acid (1.5 g), 10% palladium on activated carbon (0.65 g), ethanol 95% (100 ml), glacial acetic acid (30 ml) and concentrated hydrochloric acid (10 ml) is hydrogenated for 8 hours at room temperature in a Parr-Burgess low pressure apparatus at an initial pressure of 50 psi. At the end of this time the theoretical amount of hydrogen has been absorbed. The catalyst is filtered off, washed with 95% ethanol, and the solution is evaporated under reduced pressure. The solid residue is crystallized from 95% ethanol-ethyl ether mixture, giving 1.4 g of 5,6,7,8-tetrahydro-7-(1H-imidazol-1-yl)-8-methyl-2-naphthalenecarboxylic acid hydrochloride.

By proceeding analogously, the following compounds can be prepared:

5,6,7,8-tetrahydro-8-ethyl-7-(1H-imidazol-1-yl)-2-naphthalenecarboxylic acid hydrochloride;

5,6,7,8-tetrahydro-7-(1H-imidazol-1-ylmethyl)-8-methyl-2-naphthalenecarboxylic acid hydrochloride; and 3,4-dihydro-3-(1H-imidazol-1-ylmethyl)-4-methyl-2H-1-benzothiopyran-6-carboxylic acid hydrochloride.

After treatment with a stoichiometric amount of sodium bicarbonate the following compounds can be prepared:

5,6,7,8-tetrahydro-7-(1H-imidazol-1-yl)-8-methyl-2-naphthalenecarboxylic acid
m.p. 283°–285° C.
T.L.C. eluent CHCl$_3$:CH$_3$OH:CH$_3$COOH=85:15:0.5
Rf=0.36

5,6,7,8-tetrahydro-7-(1H-imidazol-1-ylmethyl)-8-methyl-2-naphthalenecarboxylic acid
m.p. 259°–261° C.

EXAMPLE 4

A solution of 3,4-dihydro-3(1H-imidazol-1-ylmethyl)-4-hydroxy-2H-1-benzopyran-6-carboxylic acid (3.0 g) in glacial acetic acid (60 ml) and concentrated sulfuric acid (30 ml) is heated at 80° C. for 3 hours. After cooling, the reaction mixture is poured into crushed ice, neutralized with ammonium hydroxide and extracted with methylene chloride. The organic layer is dried over sodium sulfate and evaporated to dryness. The resulting residue is treated with ethyl ether to give 1.5 g of 3-(1H-imidazol-1-ylmethyl)-2H-1-benzopyran-6-carboxylic acid, m.p. 258°–259°.

Elemental analysis: Found: C 65.58; H 4.70; N 10.96. Calculated for C$_{14}$H$_{12}$N$_2$O$_3$: C 65.62; H 4.72; N 10.93.

N.M.R. (CF$_3$COOD) ppm: 4.91 (2H, s, CH$_2$N), 5.06 (2H, s, OCH$_2$) 6.68 (1H, broad s, H-4), 6.98–8.80 (6H, m, phenyl and imidazole).

Analogously, the following compounds can be prepared:

5,6-dihydro-7-(1H-imidazol-1-ylmethyl)-2-naphthalenecarboxylic acid, m.p. 298°–300° C.
Elemental analysis: Found: C 70.70; H 5.55; N 10.98. Calculated for C$_{15}$H$_{14}$N$_2$O$_2$: C 70.90; H 5.51; N 11.00.
TLC: eluant CHCl$_3$: CH$_3$OH:CH$_3$COOH = 100:45:5
Rf=0.67
N.M.R. (DMSO-d$_6$) δ ppm: 2.27 (2H, t, CH$_2$CH$_2$C=CH), 2.91 (2H, t, CH$_2$ —CH$_2$C=CH) 5.07 (2H, s, CH$_2$N), 6.56 (1H, s, —$\overline{\text{H}}$C=C-CH$_2$CH$_2$), 7.24–9.22 (6H, m, phenyl and imidazole).

3-(1H-imidazol-1-ylmethyl)-2H-1-benzothiopyran-6-carboxylic acid;

3-(1H-imidazol-1-ylmethyl)-2-methyl-2H-1-benzothiopyran-6-carboxylic acid;
Elemental analysis: Found: C 63.4; H 4.90; N 9.85; S 11.40. Calculated for C$_{15}$H$_{14}$N$_2$O$_2$S: C62.92; H 4.93; N 9.78; S 11.20.
TLC: eluant CH$_2$Cl$_2$:CH$_3$OH:CH$_3$COOH=80:20:0.5
Rf=0.45
N.M.R. (DMSO-6) δ p.p.m.:
1.04 (d, 3H); 3.5 (q, 1H); 4.87 (broad s, 2H); 6.43 (broad s, 1H);
6.95 (dd, 1H); 7.22 (dd, 1H); 7.35 (dd, 1H); 7.6–7.8 (m, 3H); 3-(1H-imidazol-1-ylmethyl)-2-methyl-2H-1-benzopyran-6-carboxylic acid;

ethyl 3-(1H-imidazol-1-ylmethyl)-2H-1-benzothiopyran-6-carboxylate;

ethyl 5,6-dihydro-7-(1H-imidazol-1-ylmethyl)-2-naphthalenecarboxylate; and 3-(1H-imidazol-1-ylmethyl)-2H-1-benzothiopyran-6-methanol.

The 3,4-dihydro-3-(1H-imidazol-1-ylmethyl)-4-hydroxy-2H-1-benzopyran-6-carboxylic acid used above is prepared as follows: NaBH$_4$ (4.2 g) is added portionwise to a solution of 3,4-dihydro-3-(1H-imidazol-1-ylmethyl)-4-oxo-2H-1-benzopyran-6-carboxylic acid (10 g) in methanol (500 ml) at 10°–15° C. The mixture, stirred at room temperature for 2 hours, is added with water (600 ml) and neutralized with hydrochloric acid. The solution is exctracted with CHCl$_3$ and the organic solvent is dried and evaporated to dryness giving 6.6 g of 3,4-dihydro-3-(1H-imidazol-1-ylmethyl)-4-hydroxy-2H-1-benzopyran-6-carboxylic acid. m.p. 265° (dec).

Elemental analysis: Found: C 61.22; H 5.15; N 10.23. Calculated for $C_{14}H_{14}N_2O_4$: C 61.30; H 5.14; N 10.21.

The 3,4-dihydro-3-(1H-imidazol-1-ylmethyl)-4-oxo-2H-1-benzopyran-6-carboxylic acid used above is prepared from the corresponding Mannich base hydrochloride (27.8 g) [3,4-dihydro-3-N,N dimethylaminomethyl-4-oxo-2H-1-benzopyran-6-carboxylic acid hydrochloric, p.f. 200° (dec)] and imidazole (66.2 g) in water (280 ml).

The mixture is stirred at room temperature for 3 hours and evaporated to dryness. The residue, treated with methanol-ethyl ester, gives 20 g of 3,4-dihydro-3-(1H-imidazol-1-ylmethyl)-4-oxo-2H-1-benzopyran-6-carboxylic acid, m.p. 205° C. (dec).

Found: C 61.58; H 4.45; N 10.31. Calculated for $C_{14}H_{12}N_2O_4$: C 61.76; H 4.44; N 10.29.

EXAMPLE 5

A mixture of 3-(1H-imidazol-1-ylmethyl)-2H-1-benzopyran-6-carboxylic acid (0.6 g), palladium 10% on activated carbon (0.3 g), ethanol 95% (50 ml), glacial acetic acid (25 ml) and concentrated hydrochloric acid (5 ml) is hydrogenated for 7 h at room temperature in a Parr-Burgess low pressure hydrogenator at an initial pressure at 50 psi.

At the end of this time the theoretical amount of hydrogen has been absorved.

The catalyst is filtered off and the solution is evaporated under reduced pressure.

The solid residue is treated with ethanol 99% and ethyl ether to give:

0,6 g of 3,4-dihydro-3-(1H-imidazol-1-ylmethyl)-2H-1-benzopyran-6-carboxylic acid hydrochloride, m.p. 270° C. (dec).

Elemental Analysis: Found: C 56.96; H 5.14; N 9.52; Cl 12.02. Calculated for $C_{14}H_{15}Cl N_2O_3$: C 57.05; H 5.13; N 9.50; Cl 11.98.

N.M.R. (DMSO-d6) δ p.p.m.: 2.7 (3H, m, CH—$CH_2$) 3.8–4.5 (4H, m, $OCH_2$ and $NCH_2$), 6.84–7.7 (5H, m, benzene H and NCHCHN), 9.25 (1H, broad s, NCHN).

Analogously, the following compounds can be prepared:
3,4-dihydro-3-(1H-imidazol-1-ylmethyl)-2H-1-benzothiopyran-6-carboxylic acid hydrochloride;
3,4-dihydro-3-(1H-imidazol-1-ylmethyl)-2-methyl-2H-1-benzothiopyran-6-carboxylic acid hydrochloride; and
ethyl 3,4-dihydro-3-(1H-imidazol-1-ylmethyl)-2H-1-benzopyran-6-carboxylate hydrochloride.

EXAMPLE 6

Methyltriphenylphosphonium iodide (5,68 g) is added portionwise with stirring, under dry nitrogen, at room temperature to a mixture of potassium tert-butylate (1,58 g) and dry tetrahydrofuran (60 ml).

The mixture is stirred at room temperature for 30 minutes, then a solution of ethyl 5,6,7,8-tetrahydro-7-(1H-imidazol-1-yl)-8-oxo-2-naphthalenecarboxylate (2.0 g) in dry tetrahydrofuran (60 ml) is added portionwise.

After stirring at 40° C. for 3 hours, the reaction mixture is filtered and evaporated to dryness. The residue is taken up with methylene chloride, the resulting solution is washed with water and extracted with hydrochloric acid 8%. The acidic aqueous layers were combined, neutralized with sodium bicarbonate and extracted with methylene chloride. The organic layer is dried over sodium sulfate and evaporated to give a solid residue which was chromatographed on a silica gel column, eluiting with methylene chloride-methanol (20:1).

The eluate, evaporated to dryness yielded 1.1 g of ethyl 5,6,7,8-tetrahydro-7-(1H-imidazol-yl)-8-methylene-2-naphthalenecarboxylate.

Elemental analysis: Found: C 72.02; H 6.43; N 9.89. Calculated for $C_{17}H_{18}N_2O_2$: C 72.32; H 6.42; N 9.92.

N.M.R. (CDCl3) ppm: 1.41 (3H, t, $CH_3$); 2.2–2.5 (2H, m, $CH_2$—CH); 3.0 (2H, m, $CH_2$—$\phi$); 4.40 (2H, q, $OCH_2$); 4.87 (1H, d, —CH); 5.01 (1H, m, CH—N); 5.86 (1H, d, =CH); 6.95–8.36(6H, m, phenyl and imidazole).

By proceeding analogously, the following compounds can be prepared:
tert-Butyl 5,6,7,8-tetrahydro-7-(1H-imidazol-1-yl)-8-methylene-2-naphthalenecarboxylate;
Ethyl 5,6,7,8-tetrahydro-8-ethylidene-7-(1H-imidazol-1-yl)-2-naphthalenecarboxylate;
tert-Butyl 5,6,7,8-tertrahydro-8-ethylidene-7-(1H-imidazol-1-ylmethyl)-2-naphthalenecarboxylate, and
tert.Butyl 5,6,7,8-tetrahydro-7-(1H-imidazol-1-ylmethyl)-8-methylene-2-naphthalenecarboxylate.

EXAMPLE 7

A mixture of ethyl 5,6,7,8-tetrahydro-7-(1H-imidazol-1-yl)-8-methylene-2-naphthalenecarboxylate (0.46 g), sodium hydroxide (0.8 g), ethanol (40 ml) and water (5 ml) is heated under reflux for 2 hours. The solution is evaporated, the residue is dissolved in water and the solution, acidified with acetic acid, is extracted with methylene chlorid. The organic layer is dried over sodium sulfate and evaporated to give 0.35 g of 5,6,7,8-tetrahydro-7-(1H-imidazol-1-yl)-8-methylene-2-naphthalenecarboxylic acid.

m.p. 227°–229° C.

Elemental analysis: Found: C 70.48; H 5.62; N 10.90. Calculated for $C_{15}H_{14}N_2O_2$: C 70.85; H 5.55; N 11.01.

N.M.R. (DMSO-d6) rpm: 2.25 (2H, m, $CH_2$—CH); 2.90 (2H, m, $CH_2$—$\phi$); 4.50 (1H, d, =CH); 5.15 (1H, dd, CHN); 5.80 (1H, d, =CH); 6.92–8.20 (6H, m, phenyl and imidazol).

T.L.C.: eluant $CH_2Cl_2:CH_3OH:CH_3COOH$=190:20:5 Rf=0.45.

By proceeding analogously, the following compounds can be prepared: 5,6,7,8-tetrahydro-8-ethylidene-7-(1H-imidazol-1-ylmethyl)-2-naphthalenecarboxylic acid.

Elemental analysis: Found: C 71.96; H 6.39; N 9.88. Calculated for $C_{17}H_{18}N_2O_2$: C 72.32; H 6.42; N 9.92.

5,6,7,8-tetrahydro-7-(1H-imidazol-ylmethyl)-8-methylene-2-naphthalenecarboxylic acid; and
5,6,7,8-tetrahydro-8-ethylidene-7-(1H-imidazol-1-yl)-2-naphthalenecarboxylic acid.

EXAMPLE 8

A solution of 5,6,7,8-tetrahydro-7-(1H-imidazol-1-yl))-8-methylene-2-naphthalenecarboxylate (2.1 g) in trifluoroacetic acid (100 ml) is refluxed for 40 hours. After cooling the solvent is evaporated under reduced pressure and the residue is dissolved in water. The solution is basified with diluited NaOH, then acidified with acetic acid. The solid precipitated is filtered, washed with water and dried to give 2.0 g of 5,6-dihydro-7-(1H-imidazol-1-yl)-8-methyl-2-naphthalenecarboxylic acid, m.p. 241°–243° C. (dec.).

By proceeding analogously, the following compounds can be prepared:
5,6-dihydro-7-(1H-imidazol-1-ylmethyl)-8-methyl-2-naphthalenecarboxylic acid; and
5,6-dihydro-8-ethyl-7-(1H-imidazol-1-yl)-2-naphthalenecarboxylic acid.

EXAMPLE 9

To a suspension of anhydrous magnesium (0.23 g) and a small crystal of iodine in anhydrous diethyl ether (3 ml) a solution of methyl iodide (1.3 g) in anhydrous diethyl ether (6 ml) is added dropwise. The mixture is refluxed for 1 hour then cooled to room temperature. To this mixture a solution of tert-butyl 5,6,7,8-tetrahydro-7-(1H-imidazol-1-ylmethyl)-8-oxo-2-naphthalenecaboxylate (1.0 g) in anhydrous tetrahydrofuran (25 ml) is added dropwise. The reaction mixture, after stirring at room temperature for 2 hours, is poured into water, neutralized with diluited hydrochloric acid and extracted with methylene chloride. The organic layer is dried over sodium sulfate and evaporated to dryness. The residue is taken up with trifluoracetic acid and refluxed for 45 minutes. The resulting solution is evaporated under reduced pressure and the residue is purified by silica gel column chromatography, eluiting with methylene chloride-methanol-acetic acid (180:20:2), to give 0.6 g of 5,6-dihydro-7-(1H-imidazol-1-ylmethyl)-8-methyl-2-naphthalenecarboxylic acid
m.p. 278°–280° C. Elemental analysis: Found: C 71.01; H 5.99; N 10.40. Calculated for: $C_{16}H_{16}N_2O_2$: C 71.62; H 6.01; N 10.44.
N.M.R. (DMSO-$d_6$)ppm 2.05 (2H, m, $CH_2$—$CH_2$—C≡C); 2.20 (3H, s, $CH_3$—C≡C); 2.70 (2H, m, $CH_2\phi$); 4.89 (2H, s, $CH_2N$); 6.87–7.88 (6H, m, phenyl and imidazole).
T.L.C.: eluant $CH_2Cl_2$:$CH_3OH$:$CH_3COOH$ = 190:20:5 Rf=0.27

By proceeding analogously, the following compound can be prepared:
5,6-dihydro-8-ethyl-7-(1H-imidazol-1-ylmethyl)-2-naphthelenecarboxylic acid
m.p. 257°–260° C.
Elemental analysis: Found: C 72.02; H 6.44; N 9.89. Calculated for: $C_{17}H_{18}N_2O_2$: C 72.32; H 6.42; N 9.92.
N.M.R. (DMSO-$d_6$) ppm: 1.07 (3H, t, $CH_3$—$CH_2$); 1.98 (2H, t, $CH_2$—C≡); 2.65 (4H, m, $CH_2\phi$, $CH_2$—$CH_3$); 4.83 (2H, s, $CH_2N$); 6.87–8.02 (6H, m, phenyl and imidazole).
7.8-dihydro-6-(1H-imidazol-1-ylmethyl)-5-methyl-2-naphthalenecarboxylic acid.

EXAMPLE 10

To a suspension in dry benzene (25 ml) of 5,6-didhydro-7-(1H-imidazol-1-yl)-8-methyl-2-napthalenecarboxylic acid (0.5 g), oxahyl chloride (0.37 ml) was added dropwise under cooling in an ice bath.

The reaction mixture wad stirred 2 hours at 8°–10° C. and then evaporated to dryness under reduced pressure.

The residue was dissolved in anhydrous DMF (15 ml) and gaseous $NH_3$ was formed through the solution with stirring and cooling in an ice bath for 5 hours.

The reaction mixture was evaporated to dryness under reduced pressure. $1^N$NaOH was added to the residue and extracted with ethyl acetate.

The organic phase, dried on $Na_2SO_4$ and filtered was evaporated to dryness and the residue taken up with ethylether and filtered to give 5,6-dihydro-7-(1H-imidazol-1-yl)-8-methyl-2-naphthalenecarboxamide (0.24), m.p. 207°–10° C.
Elemental analysis: Found: C 70.16; H 6.04; N 15.69. Calculated for $C_{15}H_{15}N_3O_4$: C 71.12; H 5.96; N 16.58.
TLC eluant $CHCl_3$:$CH_3OH$ (80:20) Rf=0.53
N.M.R. (DMSO-$d_6$) ppm: 1.95 (3H, t, $CH_3$); 2.61 (2H, m, $CH_2$—C≡); 2.98 (2H, t, $CH_2$—$\phi$); 7.03–8.01 (8H, m, phenyl, imidazole and $CONH_2$).

EXAMPLE 11

To a solution of hydrogen chloride in absolute ethanol (50 ml), 5,6-dihydro-7-(1H-imidazol-1-yl)-8-methyl-2-naphthalenecaboxylic acid hydrochloride, (0.5 g) was added.

The reaction mixture wad heated at 60° C. for 3 hours and then evaporated under reduced pressure to dryness.

The residue, taken up with ethylether and filtered to give ethyl 5,6-dihydro-7-(1H-imidazol-1-yl)-8-methyl-2-naphthalenecaboxylate hydrochloride (0.45 g), m.p. 202°–3° C.
Elemental analysis: Found: C 62.89; H 6.02; N 8.45; Cl 10.73. Calculated for: $C_{17}H_{18}NO_2O_2$; HCl: C 64.04; H 6.00; N 8.78; Cl 11.12.
TLC eluant $CHCl_3$:$CH_3OH$:$CH_3COOH$ (45:5:0.5) Rf=0.67.
N.M.R. (DMSO-$d_6$) ppm 1.32 (3H, t, $COOCH_2CH_3$); 1.98 (3H, t, $CH_3$—C≡); 2.71 (2H, m, $CH_2$—C≡); 3.08 (2H, t, $CH_2$—$\phi$). 4.32 (2H, q, $COOCH_2$); 7.44–9.29 (6H, m, phenyl and imidazole).

By proceeding analogously the following compound can be prepared:
ethul 5,6-dihydro-7-(1H-imidazol-1-ylmethyl)-8-methyl-2-naphthalenecaboxylate hydrochloride.

After treatment with the stoichiometric of sodium bicarbonate the following compounds can be obtained
ethyl 5,6-dihydro-7-(1H-imidazol-1-yl)-8-methyl-2-naphthalenecarboxylate;
ethyl 5,6-dihydro-7-(1H-imidazol-1-ylmethyl)-8-methyl-2-naphthalenecarboxlate.

EXAMPLE 12

A suspension of 5,6-dihydro-7-(1H-imidazol-1-yl)-8-methyl-2-naphthalenecarboxylic acid (0,5 g) in abs. ethanol (40 ml) is treated with 37% hydrochloric acid (0.2 ml) and added up with diethylether.

The precipitate is filtered and washed and diethylether to give 0.41 g of 5,6-dihydro-7-(1H-imidazol-1-yl)-8-methyl-2-naphthalenecarboxlic acid.hydrochloride.

EXAMPLE 13

0.5 g of 5,6-dihydro-7-(1H-imidazol-1-yl)-8-methyl-2-naphthalenecarboxylic acid are added, under stirring, to 39 ml of 0.05N NaOH and the pH of the solution adjusted with few drops of 0.05N NaOH till a clear solution is obtained.

The solution is then evaporated under reduced pressure and the residue is dried in the oven at 90° C. in vacuo thus giving the 5,6-dihydro-7-(1H-imidazol-1-yl)-8-methyl-2-naphthalenecarboxylic acid sodium salt.

EXAMPLE 14

Tablets, each weighing 150 mg and containing 50 mg of the active substance can be manufactured as follows:

| Composition (for 10,000 tablets) | |
|---|---|
| 5,6-dihydro-7-(1H-imidazol-1-yl)-8-methyl-2-naphthalenecarboxylic acid | 500 g |
| Lactose | 710 g |
| Corn starch | 237.5 g |
| Talc powder | 37.5 g |
| Magnesium stearate | 15 g |

5,6-dihydro-7-(1H-imidazol-1-yl)-8-methyl-2-naphthalenecarboxylic acid, lactose and a half of the corn starch are mixed; the mixture is then forced through a sieve of 0.5 mm openings. Corn starch (18 mg) is suspended in warm water (180 ml). The resulting paste is used to granulate the power. The granules are dried, comminuted on a sieve of sieve size 1.4 mm, then the remaining quality of starch, talc and magnesium are added, carefully mixed, and processed into tablets using punches of 8 mm diameter.

We claim:

1. A compound of formula (I)

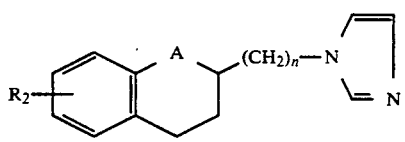

wherein
A is a $\geq CR_3$ or $>CHR_3$ group in which $R_3$ is $C_1$–$C_4$ alkyl;
n is zero or 1; and
$R_2$ is a —$CONH_2$ or —$COOR^1$ group in which $R^1$ is hydrogen or $C_1$–$C_4$ alkyl;
or a pharmaceutically acceptable salt thereof.

2. A compound of formula (I) according to claim 1, wherein A is a $\geq CR_3$ group in which $R_3$ is $C_1$–$C_4$ alkyl; n is zero or 1; and
$R_2$ is a —$CONH_2$ or —$COOR^1$ group in which $R^1$ is hydrogen or $C_1$–$C_4$ alkyl; or a pharmaceutically acceptable salt thereof.

3. A compound of formula (I) according to claim 1 selected from the group consisting of:

5,6-dihydro-7-(1H-imidazol-1-yl)-8-methyl-2-naphthalenecarboxylic acid;
5,6-dihydro-8-ethyl-7-(1H-imidazol-1-yl)-2-naphthalenecarboxlic acid;
5,6-dihydro-7-(1H-imidazol-1-ylmethyl)-8-methyl-2-naphthalenecarboxylic acid;
5,6,7,8-tertrahydro-7-(1H-imidazol-1-ylmethyl)-8-methyl-2-naphthalenecarboxylic acid;
ethyl 5,6-dihydro-7-(1H-imidazol-1-yl)-8-methyl-2-naphthalenecarboxylate;
5,6-dihydro-7-(1H-imidazol-1-yl)-8-methyl-2-naphthalenecarboxamide;
ethyl 5,6-dihydro-7-(1H-imidazol-1-ylmethyl)-8-methyl-2-naphthalenecarboxylate;
5,6-dihydro-8-ethyl-7-(1H-imidazol-1-ylmethyl)-2-naphthalenecarboxylic acid;
7,8-dihydro-6-(1H-imidazol-1-ylmethyl)-5-methyl-2-naphthalenecarboxylic acid;
or the pharmaceutically acceptable salt thereof.

4. A pharmaceutical composition containing a suitable carrier and/or diluent and, as an active principle, a pharmaceutically effective amount of a compound of formula (I) as define in claim 1, or a pharmaceutically acceptable salt thereof.

5. A method for the treatment of a disease related to an enhancement of thromboxane $A_2$ synthesis, the method comprising administering to a patient in need of such treatment a pharmaceutically effective amount of a compound of formula (I) as define in claim 1, or a pharmaceutically acceptable salt thereof.

6. A method for the treatment of nephropathies, the method comprising administering to a patient in need of such treatment a pharmaceutically effective amount of a compound of formula (I) as defined in claim 1, or a pharmaceutically acceptable salt thereof.

7. A method for the prevention and/or treatment of cyclosporin A-induced nephrosis, the method comprising administering to a patient in need of such treatment a pharmaceutically effective amount of a compound of formula (I) as define in claim 1, or a pharmaceutically acceptable salt thereof.

8. A method for the treatment of hyperlipidaemia secondary to nephrotic syndrome, the method comprising administering to a patient in need of such treatment a pharmaceutically effective amount of a compound of formula (I) as defined in claim 1, or a pharmaceutically acceptable salt thereof.

* * * * *

UNITED STATES PATENT AND TRADEMARK OFFICE
CERTIFICATE OF CORRECTION

PATENT NO. : 5,204,364
DATED : April 20, 1993
INVENTOR(S) : Carganico et al.

It is certified that error appears in the above-identified patent and that said Letters Patent is hereby corrected as shown below:

Title page, item [57],
In the Abstract, line 6, change "$\geqq$" to -- $\geqslant$ --.
Column 1, line 26, change "$\geqq$" to -- $\geqslant$ --; and
line 42, change "$\geqq$" to -- $\geqslant$ --.
Column 2, line 16, change "$\geqq$" to -- $\geqslant$ --; and
line 29, change "$\geqq$" to -- $\geqslant$ --.
Column 3, line 12, change "$\geqq$" to -- $\geqslant$ --; and
line 54, change "$\geqq$" to -- $\geqslant$ --.
Column 19, line 34, change "$\geqq$" to -- $\geqslant$ --; and
line 41, change "$\geqq$" to -- $\geqslant$ --.

Signed and Sealed this

Twenty-eighth Day of June, 1994

Attest:

BRUCE LEHMAN

*Attesting Officer*     *Commissioner of Patents and Trademarks*